United States Patent
Nord et al.

(10) Patent No.: US 8,693,630 B2
(45) Date of Patent: Apr. 8, 2014

(54) METHOD AND APPARATUS PERTAINING TO RADIATION-THERAPY TREATMENT-PLAN OPTIMIZATION

(75) Inventors: Janne Nord, Espoo (FI); Lasse Toimela, Espoo (FI); Marko Rusanen, Helsinki (FI)

(73) Assignee: Varian Medical Systems International AG, Zug (CH)

( * ) Notice: Subject to any disclaimer, the term of this patent is extended or adjusted under 35 U.S.C. 154(b) by 673 days.

(21) Appl. No.: 12/987,293

(22) Filed: Jan. 10, 2011

(65) Prior Publication Data

US 2012/0175530 A1   Jul. 12, 2012

(51) Int. Cl.
*A61N 5/10*        (2006.01)
*A61B 6/03*        (2006.01)

(52) U.S. Cl.
USPC ............................................. 378/65; 378/901

(58) Field of Classification Search
USPC ........... 378/4–20, 65, 210, 901; 600/425–429
See application file for complete search history.

(56) References Cited

U.S. PATENT DOCUMENTS

| | | | |
|---|---|---|---|
| 2008/0177179 A1* | 7/2008 | Stubbs et al. | 600/431 |
| 2010/0094119 A1* | 4/2010 | Yu et al. | 600/411 |
| 2012/0059243 A1* | 3/2012 | Vortman et al. | 600/411 |

* cited by examiner

*Primary Examiner* — Anastasia Midkiff
(74) *Attorney, Agent, or Firm* — Fitch, Even, Tabin & Flannery LLP

(57) ABSTRACT

These various embodiments access target information regarding a radiation-therapy treatment volume for a given patient as well as non-target information regarding at least one structure other than the radiation-therapy treatment volume that also comprises a part of the given patient. These embodiments then provide for accessing uncertainties information regarding spatial uncertainties as pertain to at least one of the target information and the non-target information and using that uncertainties information to characterize at least one radiation-therapy treatment plan optimization consideration with respect to a preference of usage to thereby provide preference considerations. These preference considerations are then used to influence a follow-on radiation-therapy treatment plan optimization process when developing a treatment plan for the radiation-therapy treatment volume.

23 Claims, 2 Drawing Sheets

METHOD AND APPARATUS PERTAINING TO RADIATION-THERAPY TREATMENT-PLAN OPTIMIZATION

TECHNICAL FIELD

This invention relates generally to the optimization of radiation-therapy treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. For example, many treatment plans provide for exposing the target volume to possibly varying dosages of radiation from a number of different directions. Arc therapy, for example, comprises one such approach.

Such treatment plans are often optimized prior to use, (As used herein, "optimization" will be understood to refer to improving a candidate treatment plan without necessarily ensuring that the optimized result is, in fact, the singular best solution.) Though important to the use of treatment plans, typical optimization processes are computationally intensive. This, in turn, can require the use of expensive processing platforms and/or a considerable amount of processing time. Such burdens, however, can lead to unwanted costs and/or delay for the service provider and/or the patient.

BRIEF DESCRIPTION OF THE DRAWINGS

The above needs are at least partially net through provision of the method and apparatus pertaining to radiation-therapy treatment-plan optimization described in the following detailed description, particularly when studied in conjunction with the drawings, wherein.

Figure 1:
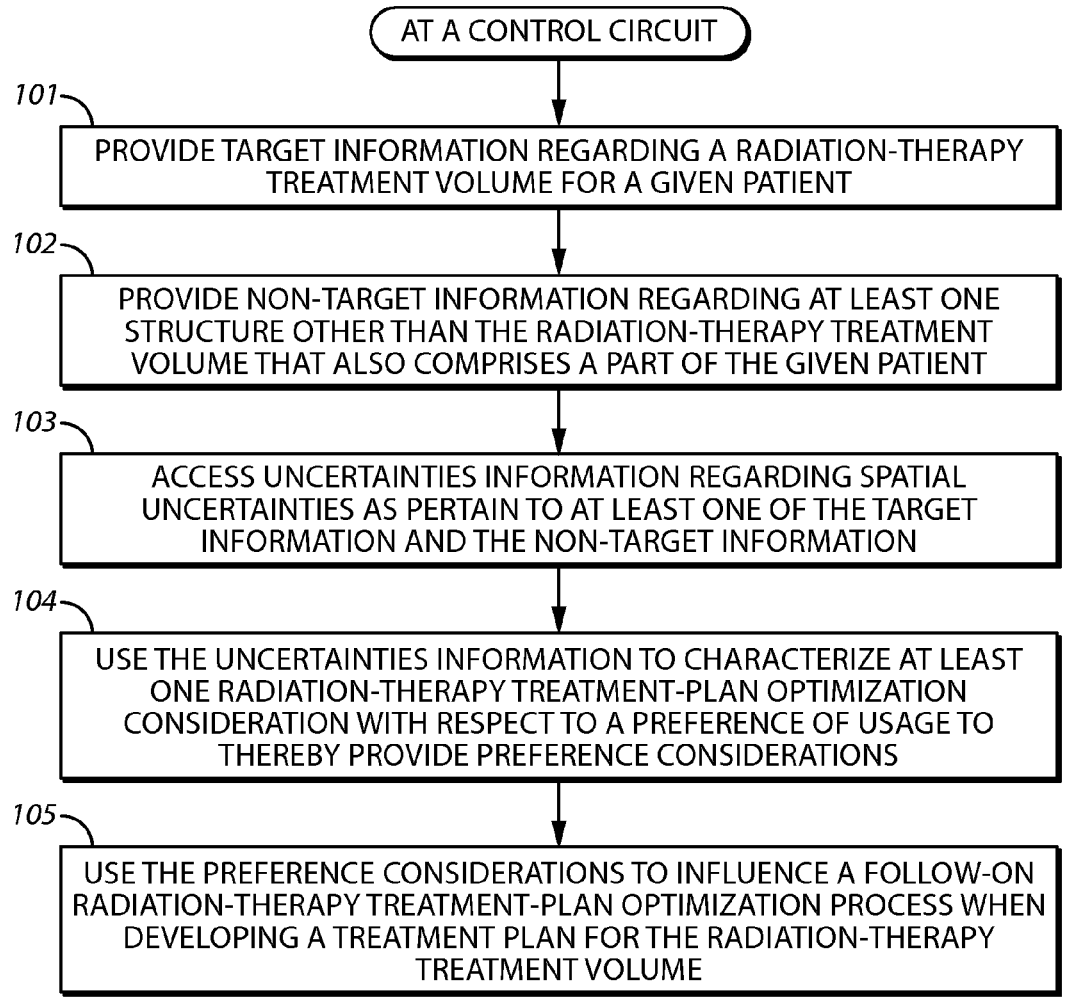
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms an expressions by persons skilled in the technical field as set forth above except where different specific meanings have otherwise been set forth herein.

DETAILED DESCRIPTION

Generally speaking, these various embodiments access target information regarding a radiation-therapy treatment volume for a given patient as well as non-target information regarding at least one structure other than the radiation-therapy treatment volume that also comprises a part of the given patient. These embodiments then provide for accessing uncertainties information regarding spatial uncertainties as pertain to at least one of the target information and the non-target information and using that uncertainties information to characterize at least one radiation-therapy treatment plan optimization consideration with respect to a preference of usage to thereby provide preference considerations. These preference considerations are then used to influence a follow-on radiation-therapy treatment plan optimization process when developing a treatment plan for the radiation-therapy treatment volume.

By one approach, one or both of the target information and the non-target information can comprise (at least in part) values expressed in Hounsfield Units. In such a case, if desired, the aforementioned uncertainties information can comprise, at least in part, uncertainties with respect to the accuracy of those values.

By one approach, the aforementioned preference considerations can comprise considerations that represent a relatively greater treatment-plan sensitivity to the noted spatial uncertainties. For example, one or more of these preference considerations can represent a preference (such as a negative or reduced preference) with respect to a particular radiation-beam directionality (such as, and without intending any limitations in these regards, a reduced or negative preference with respect to a particular radiation-beam directionality that presents a relatively higher risk to the aforementioned at least one structure (given the aforementioned spatial uncertainties). This, in turn, can yield an approach that is more robust in the face of such spatial uncertainties.

By one approach, assessing the uncertainties information regarding spatial uncertainties can comprise assessing such information with respect to time as pertain to the target information and/or the non-target information. This can comprise, for example, consideration of a window of time that comprises a single course of radiation therapy. As another example, this can comprise consideration of a window of time that spans a course of a plurality of radiation-therapy dosages.

So configured, a given optimization process can often be expected to converge more quickly upon a satisfactory treatment plan and/or to yield a better plan in a same amount of time than one might ordinarily expect. In particular, these teachings can serve to influence a given optimization process to avoid using or exploring particular treatment plan settings (such as, for example, particular field angles when employing an arc therapy platform) that might otherwise be considered.

These teachings are readily employed with numerous existing optimization approaches and hence can serve to leverage the value of such approaches. These teachings are also highly flexible in practice and can serve, for example, when applied both with photon-based treatments as well as radiation-therapy treatments that employ proton beams. In many cases these teachings are readily enabled via programming of existing platforms and hence can be implemented in an economical manner, both with new platforms as well as with legacy equipment.

These and other benefits may become clearer upon making a thorough review and study of the following detailed description. Referring now to the drawings, and in particular to FIG. 1, an illustrative process 100 that is compatible with many of these teachings will now be presented. Generally speaking, a control circuit of choice can carry out this process 100. Further details in these regards will be provided below.

At step 101 this process 100 provides target information regarding a radiation-therapy treatment volume for a given patient. This can comprise, but is not limited to, information regarding, for example, a general or specific geometric characterization of the volume, specific dimensions (such as length, width, height, and so forth), segmentation characterization regarding part or all of the volume, location and/or orientation of the treatment volume within the given patient, and so forth. By one approach, this information can comprise (in whole or in part) values that are expressed in Hounsfield Units (such units comprising a well-understood area of endeavor).

At step 102 this process 100 provides non-target information regarding at least one structure other than the aforementioned radiation-therapy treatment volume. This structure also comprises a part of the given patient (such as a particular organ that may be located very close to the treatment target). Such non-target information can comprise, but is not limited to, information regarding, for example, a general or specific geometric characterization of the structure, specific dimensions (such as length, width, height, and so forth), segmentation characterization regarding part or all of the structure, location and/or orientation of the structure within the given patient and/or with respect to the aforementioned treatment volume, and so forth. By one approach, this information can also comprise (in whole or in part) values depicting mass density such as Hounsfield Units, stopping power or electron density.

This process 100 accesses (at step 103) uncertainties information regarding this information regarding one or both of the target and the non-target structure(s). By one approach, this uncertainties information reflects spatial uncertainties as pertain to the target and/or non-target information. As one relevant but non-limiting example in these regards, when the target and/or non-target information comprises, in whole or in part, values depicting mass density such as Hounsfield Units, stopping power or electron density, this uncertainties information can comprise information regarding uncertainties with respect to the accuracy of those values. This can comprise general information (such as knowing that mass density values derived using a particular imaging process tend to be accurate within plus-or-minus a particular number of units, percentage points, or the like) and/or specific information such as knowing that the values for certain materials are more or less accurate than the values for other materials) as may be available.

Generally speaking, at least the bulk of this uncertainties information will comprise, in a given application setting, information know well prior to a need to access such information for these purposes. Such information might be gleaned, for example, from published specifications for a given imaging platform and/or image-data processing software. As another example, such information might be developed, in whole or in part, through empirical testing and/or observation of the imaging platform(s) used to provide one or both of the aforementioned target and non-target information.

These teachings will accommodate using uncertainties information regarding a wide variety of informational perspectives (such as, for example, materials identification and so forth). Generally speaking, however, these teachings at least rely upon the spatial uncertainties noted above. In many application settings, this refers to uncertainties regarding the boundaries of the radiation-therapy treatment volume and/or the other structure(s) and/or the proximity and/or orientation of the former with respect to the latter. As one simple example in these regards, when considering how close a target volume (such as a tumor) is to a healthy organ to be protected from radiation, this uncertainties information can reflect an understanding regarding the likely or possible accuracy of that proximity consideration.

By one approach, the aforementioned uncertainties information can be temporally insensitive. In such a case, the uncertainties information may be applicable and relevant without regard to a particular timeframe. By another approach, however, some or all of the uncertainties information can be temporally sensitive. As one example in these regards, the uncertainties information can pertain to spatial uncertainties over time as pertain to at least one of the target information and the non-target information. By one approach, this "time" can comprise time over a course of a radiation-therapy treatment dosing (such as a single radiation-therapy treatment session for the given patient). By another approach, this "time" can comprise time over a course of a plurality of radiation-therapy dosings (as carried out, for example, in different treatment sessions on different days over a period of days, weeks, or months).

At step 104 this process 100 utilizes this uncertainties information to characterize at least one radiation-therapy treatment plan optimization consideration with respect to a preference of usage. This, in turn, yields one or more corresponding preference considerations. At step 105 this process 100 can then use these preference considerations to influence a follow-on radiation-therapy treatment-plan optimization process when developing a treatment plan for the aforementioned radiation-therapy treatment volume.

Some specific examples in these regards may be helpful. In providing these examples, however, it will be understood that no particular limitations with respect to the practice of these teachings are intended nor are the specifics of these examples intended to comprise an exhaustive listing of all such possibilities in these regards.

Per a first example, a radiation-therapy treatment volume appears in close proximity to another structure within the same patient. For the purposes of this example the radiation-therapy treatment volume will be presumed to comprise unwanted tissue such as a tumor while the other structure comprises desired biological material (such as a particular organ). It will also be presumed that the platform is able to direct a radiation beam to the radiation therapy volume from a variety of different angles. (An arc therapy-style of platform comprises one non-limiting example in such regards but these teachings will readily accommodate other possibilities as well.) Here, for the sake of clarity and simplicity, only three such available angles are considered.

A first one of these radiation-beams is capable of radiating the non-targeted structure unless properly focused with respect to the radiation-therapy treatment volume (when using, for example, a proton-based treatment platform). When sufficient uncertainty exists with respect to the true positions and boundaries of these two bodies, this can lead, in turn, to uncertainty regarding whether the non-targeted structure will be inadvertently exposed to the radiation beam notwithstanding appropriate efforts to focus the radiation beam using all available spatial information regarding these bodies.

Such concerns do not similarly burden the other two considered radiation beams. That is, if either of these radiation beams should in fact have their effect felt somewhat beyond the actual boundaries of the radiation-therapy treatment volume (due to spatial uncertainties), the non-targeted structure will nevertheless be out of harm's way.

In such a case, these teachings will accommodate, for example, using the aforementioned spatial uncertainties to exhibit relatively greater treatment-plan sensitivity to such spatial uncertainties by influencing a preference with respect to one or more particular radiation-beam directionalities. By one approach this can comprise representing a preference (for example, via a weighting mechanism) for a particular directionality. By another approach, in lieu of the foregoing or in combination therewith, this can comprise representing a prejudice (again, if desired, via a weighting mechanism) against a particular directionality. In the particular example, for example, the radiation-beam directionality that corresponds to the first radiation beam can be characterized in some negative manner of choice to discourage the treatment plan optimization process from employing this particular directionality. In the alternative, and simply as another example, the directionalities corresponding to the other radiation beams can be characterized in some positive manner of choice to encourage the treatment plan optimization process to employ these particular directionalities.

By one approach, this notion of discouraging use of a particular radiation-beam directionality can be absolute. In such a case, these teachings can serve to prevent consideration and/or use of the disadvantageous directionality by the platform that develops the treatment plan. By another approach, a less-than-absolute influence can serve. In such a case, these teachings can serve to discourage the consideration and/or use of a particular directionality without prohibiting that directionality. Such an approach may be useful in application settings where the risks presented by the spatial uncertainties are small in comparison to the problems associated with utterly prohibiting certain directionalities.

In any event, it can be seen and appreciated that these teachings will readily accommodate forming one or more preference considerations that represent a preference (absolute or relative, and direct or indirect) with respect to one or more particular radiation-beam directions that present a relatively higher risk to the non-targeted structure in view of the spatial uncertainties in play.

As suggested above, these teachings are also applicable with respect to spatial uncertainties that are temporally based. In a next illustrative example the radiation-therapy treatment volume comprises an organ (such as a lung) having moving boundaries. In many cases, this movement will tend to be more prominent in one plane of movement than another. In the present example, the movement largely occurs back and forth in a given direction.

In such a case, a radiation beam 305 parallels that direction of movement offers an increased opportunity for problems to develop due to the spatial uncertainties described above. This can pose problems both with respect to providing the radiation-therapy treatment volume with an intended dosage and with respect to protecting adjacent structures from unintended dosings/exposure.

Similarly, a radiation beam that is oriented differently (such as orthogonally to the direction of movement) is considerably less sensitive to such spatial uncertainties. In such a case, these teachings will accommodate, for example, using the aforementioned spatial uncertainties to exhibit relatively greater treatment-plan sensitivity to such spatial uncertainties by influencing (directly or indirectly) a preference with respect to radiation-beam directionalities that are other than, say, substantially parallel to the radiation-therapy treatment volume's direction of movement. (The expression "substantially parallel" can reflect the particular sensitivities as may pertain to a given application setting. This might mean, for example, "within two percent of being parallel." As another example, this might mean, "within five percent of being parallel." As yet another example, this might mean, "within twenty percent of being parallel" and so forth.)

Figure 2:
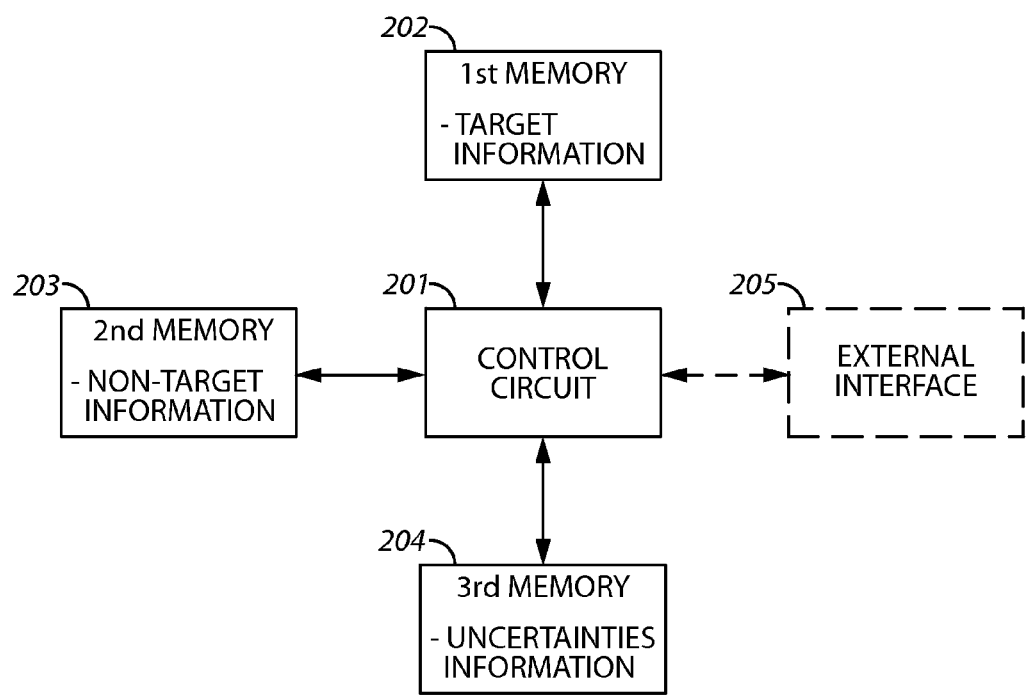
FIG. 2 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform 200 will now be provided.

In this illustrative example, a control circuit 201 operably couples to a first memory 202, a second memory 203, and a third memory 204. The first memory 202 stores the aforementioned target information, the second memory 203 stores the aforementioned non-target information, and the third memory 204 stores the aforementioned uncertainties information. This illustration can be taken literally and these three memories can comprise individual, physically-discrete components if desired. This illustration can also be taken as a logical representation, however. In this case, these memories can comprise different portions of a shared larger memory component. It will also be understood that these individually-depicted memories can each comprise a plurality of physically-discrete memory components. Such architectural variations are well understood in the art and require no further elaboration here.

The control circuit 201 can comprise a fixed-purpose hard-wired platform or can comprise a partially or wholly programmable platform. These architectural options, too, are well known and understood in the art and require no further description here. When the control circuit 201 comprises a partially or wholly programmable platform, the control circuit 201 can be configured, via corresponding programming, to carry out one or more of the steps, actions, and/or functions described herein.

By one approach, the control circuit 201 can optionally further operably couple to one or more external interfaces 205. Examples in these regards can include, but are not limited to, one or more end-user interfaces such as end-user input mechanisms (for example, keyboards, cursor-control devices, touch screens, and so forth) and end-user output mechanisms (for example, displays, printers, and so forth). By one approach, for example, this external interface 205 can provide a mechanism by which the control circuit 201 outputs the aforementioned treatment plan.

Such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, these teachings can help to address several sources of error that are often present during radiation treatments. These include various uncertainties such as uncertainties regarding the patient's position, Hounsfield Unit values (particularly when the radiation treatment makes use of a proton-delivery system), and temporally-experienced changes with respect to the patient's anatomy.

These teachings will support, for example, using one or more matrices that describe preferred (and/or un-preferred) field orientations to use during optimization. In this case, for example, a distance transform can be generated with respect to critical organs and a preferred direction can be established as being perpendicular to the gradient of the corresponding distance transform matrix (to thereby avoid unduly exposing the critical organ(s) to the excursions of the uncertainty). As another related example, a distance transform can be generated with respect to the treatment target and a preferred direction then established as being perpendicular to the gradient of the corresponding distance transform matrix (to thereby make it more likely that uncertainty-based dosages nevertheless remain within the treatment target.

As yet another example in these regards, these teachings will support using one or more matrices that describe such spatial uncertainty as regards the position of material. This matrix (or matrices) can then be employed during optimization to influence that process. For example, a deformation field generated using four-dimensional computed tomography (4DCT) to thereby represent an organ such as a lung.

In any event, by influencing the optimization process to prefer some approaches over others as a function of selected uncertainties can serve to reduce the amount of time required to produce an acceptable treatment plan and/or can yield a superior treatment plan to what might have been previously achieved.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
   providing target information regarding a radiation-therapy treatment volume for a given patient;
   providing non-target information regarding at least one structure other than the radiation-therapy treatment volume that also comprises a part of the given patient;
   accessing uncertainties information regarding spatial uncertainties as pertain to at least one of the target information and the non-target information;
   using the uncertainties information to characterize at least one radiation-therapy treatment-plan optimization consideration with respect to a preference of usage to thereby provide preference considerations;
   using the preference considerations to influence a follow-on radiation-therapy treatment-plan optimization process when developing a treatment plan for the radiation-therapy treatment volume.

2. The method of claim 1 wherein the treatment plan comprises a treatment plan to control exposure of the radiation-therapy treatment volume to a proton beam.

3. The method of claim 1 wherein the treatment plan comprises a treatment plan to control exposure of the radiation-therapy treatment volume to a photon-based treatment.

4. The method of claim 1 wherein at least one of the target information and the non-target information comprises, at least in part, values representing mass density.

5. The method of claim 4 wherein the uncertainties information comprises, at least in part, uncertainties with respect to accuracy of the values.

6. The method of claim 1 wherein the preference considerations comprise considerations that represent a relatively greater treatment-plan sensitivity to the spatial uncertainties.

7. The method of claim 6 wherein at least some of the preference considerations represent a preference with respect to a particular radiation-beam directionality.

8. The method of claim 6 wherein at least some of the preference considerations represent a preference with respect to a particular radiation-beam directionality that presents a relatively higher risk to the at least one structure given the spatial uncertainties.

9. The method of claim 1 wherein accessing uncertainties information regarding spatial uncertainties as pertain to at least one of the target information and the non-target information comprises accessing uncertainties information regarding spatial uncertainties over time as pertain to at least one of the target information and the non-target information.

10. The method of claim 9 wherein the time comprises time over a course of a radiation-therapy treatment dosage.

11. The method of claim 9 wherein the time comprises time over a course of a plurality of radiation-therapy dosages.

12. The method of claim 9 wherein the at least one preference consideration comprises a preference with respect to a particular radiation-beam directionality that is at least substantially perpendicular to a direction of the spatial uncertainty over time.

13. A apparatus comprising:
    a first memory having target information regarding a radiation-therapy treatment volume for a given patient stored therein;
    a second memory having non-target information regarding at least one structure other than the radiation-therapy treatment volume that also comprises a part of the given patient stored therein;
    a third memory having uncertainties information regarding spatial uncertainties as pertain to at least one of the target information and the non-target information stored therein:
    a control circuit operably coupled to the first, second, and third memory and configured to:
       use the uncertainties information to characterize at least one radiation-therapy treatment-plan optimization consideration with respect to a preference of usage to thereby provide preference considerations;
       use the preference considerations to influence a follow-on radiation-therapy treatment-plan optimization process when developing a treatment plan for the radiation-therapy treatment volume.

14. The apparatus of claim 13 wherein the treatment plan comprises a treatment plan to control exposure of the radiation-therapy treatment volume to a proton beam.

15. The apparatus of claim 13 wherein at least one of the target information and the non-target information comprises, at least in part, values representing mass density.

16. The apparatus of claim 15 wherein the uncertainties information comprises, at least in part, uncertainties with respect to accuracy of the values.

17. The apparatus of claim 13 wherein the preference considerations comprise considerations that represent a relatively greater treatment-plan sensitivity to the spatial uncertainties.

18. The apparatus of claim 17 wherein at least some of the preference considerations represent a preference with respect to a particular radiation-beam directionality.

19. The apparatus of claim 17 wherein at least some of the preference considerations represent a preference with respect to a particular radiation-beam directionality that presents a relatively higher risk to the at least one structure given the spatial uncertainties.

20. The apparatus of claim 13 wherein the uncertainties information comprises uncertainties information regarding spatial uncertainties over time as pertain to at least one of the target information and the non-target information.

21. The apparatus of claim 20 wherein the time comprises time over a course of a radiation-therapy treatment dosage.

22. The apparatus of claim 20 wherein the time comprises time over a course of a plurality of radiation-therapy dosages.

23. The apparatus of claim 20 wherein the at least one preference consideration comprises a preference with respect to a particular radiation-beam directionality that is at least substantially perpendicular to a direction of the spatial uncertainty over time.

* * * * *